United States Patent [19]

Fedorov et al.

[11] Patent Number: 4,978,352

[45] Date of Patent: Dec. 18, 1990

[54] PROCESS FOR PRODUCING COLLAGEN-BASED CROSS-LINKED BIOPOLYMER, AN IMPLANT FROM SAID BIOPOLYMER, METHOD FOR PRODUCING SAID IMPLANT, AND METHOD FOR HERMETIZATION OF CORNEAL OR SCLERAL WOUNDS INVOLVED IN EYE INJURIES, USING SAID IMPLANT

[76] Inventors: Svyatoslav N. Fedorov, Ulitsa Dostoevskogo, 12, kv. 32; Sergei N. Bagrov, ulitsa Startovaya, 9, korpus 2, kv. 236; Vladislav T. Trofimov, ulitsa Zelenodolskava, 17, korpus 1, kv. 53; Tatyana S. Amstislavskaya, bulvar Yana Rainisa, 43, kv. 418; Alexei V. Osipov, Leningradskoe shose, 50, kv. 233, all of Moscow, U.S.S.R.

[21] Appl. No.: 356,263

[22] Filed: May 23, 1989

[51] Int. Cl.⁵ ................. B29D 11/00; A61F 2/00; A61K 37/12

[52] U.S. Cl. ................. 606/166; 128/DIG. 8; 264/1.1; 530/356; 424/427

[58] Field of Search ................. 604/893.1, 895.1; 623/4-6; 606/166, 213, 215; 128/DIG. 8; 424/423, 427-429; 530/356; 523/106; 264/1.1, 1.4

[56] References Cited

U.S. PATENT DOCUMENTS

| | | | |
|---|---|---|---|
| 3,553,299 | 1/1971 | Thiele | 623/4 |
| 4,164,559 | 8/1979 | Miyata et al. | 424/428 |
| 4,223,984 | 9/1980 | Miyata et al. | 128/DIG. 8 |
| 4,268,131 | 5/1981 | Miyata et al. | 530/356 |
| 4,349,470 | 9/1982 | Battista | 264/1.1 |
| 4,357,274 | 11/1982 | Werner | 128/DIG. 8 |
| 4,374,121 | 2/1983 | Cioca | 424/423 |
| 4,505,855 | 3/1985 | Bruns et al. | 264/1.4 |
| 4,540,532 | 9/1985 | Petcen et al. | 264/1.1 |
| 4,581,030 | 4/1986 | Bruns et al. | 128/DIG. 8 |
| 4,772,283 | 9/1988 | White | 623/5 |
| 4,781,187 | 11/1988 | Herrick | 606/166 |
| 4,865,779 | 12/1989 | Ihn et al. | 264/1.1 |
| 4,879,072 | 11/1989 | Bourset et al. | 264/1.4 |
| 4,913,904 | 4/1990 | Fyodorov et al. | 424/427 |
| 4,931,546 | 6/1990 | Tardy et al. | 530/356 |

FOREIGN PATENT DOCUMENTS

| | | | |
|---|---|---|---|
| 0628913 | 9/1978 | U.S.S.R. | 623/4 |
| 0990221 | 1/1983 | U.S.S.R. | 623/4 |
| 1321420 | 7/1987 | U.S.S.R. | |

*Primary Examiner*—C. Fred Rosenbaum
*Assistant Examiner*—Sharon Rose
*Attorney, Agent, or Firm*—Burgess, Ryan & Wayne

[57] ABSTRACT

A process for producing a collagen-based cross-linked biopolymer is provided in which a collagen solution free of low-molecular impurities is saturated with nitrogen protoxide, its concentration is brought to maximum 80 mass percent and the solution is exposed to an ionizing radiation in a dose of 0.5 to 15 kGy. An implant for hermetization of corneal and scleral wounds involved in eye injuries prepared from said bipolymer has the shape and size that provide for complete hermetization of said wounds. The method for its preparation comprises saturation of a collagen solution free of impurities and having a concentration of 0.2 to 1.3 mass percent, with nitrous oxide, filling of a mould with said solution and its exposure to an ionizing radiation in a dose of 0.5 to 15 kGy. The resultant blank is dried to a moisture content in its biopolymer of 30 to 50 mass percent, whereupon the blank is given the shape and size of a required implant.

The method of hermetization of said wounds is carried into effect by introducing the implant shaped as a cylinder with a tapered end, with said end into an operative wound incision, fixing the implant in the wound for 1 or 2 minutes and removal of the implant portion that stands over the corneal or scleral surface.

9 Claims, No Drawings

PROCESS FOR PRODUCING COLLAGEN-BASED CROSS-LINKED BIOPOLYMER, AN IMPLANT FROM SAID BIOPOLYMER, METHOD FOR PRODUCING SAID IMPLANT, AND METHOD FOR HERMETIZATION OF CORNEAL OR SCLERAL WOUNDS INVOLVED IN EYE INJURIES, USING SAID IMPLANT

FIELD OF THE INVENTION

The present invention relates to ophthalmology and has particular reference to a process for producing a cross-linked biopolymer, an implant from said biopolymer for hermetization of corneal or scleral wounds involved in eye injuries, and a method for producing said implant, as well as a method for hermetization of corneal or scleral wounds involved in eye injuries, using said implant.

A cross-linked biopolymer produced according to the proposed process will find widespread use in making contact lenses, coatings, and implants employed in all kinds of ophthalmosurgical procedures and for conservative treatment of trophic corneal affections of various etiology. The proposed implant will also be applicable for treatment of traumatic lesions of the sclera and cornea.

DESCRIPTION OF THE PRIOR ART

At present a number of biopolymers have been utilized for ophthalmological uses, such biopolymers being based on collagen, i.e., a natural protein, being compatible with the ocular tissues and featuring low antigenicity. It is in view of producing such biopolymers that radiation resistance of collagen has been studied to establish that the radiation effect depends on the radiation dose and conditions of its application. Exposure of a collagen solution to radiation may result both in a process of cross-linking of the collagen fibrils and in a degradation process, which depends on the collagen concentration and on specificity of the cross-linkage promoters used. One prior-art collagenous gel has been produced upon collagen irradiation with an ionizing radiation in a dose of 33 kGy. A change in the electrophoretic pattern and reduced acid solubility confirm the fact that new structure-forming bonds have arisen in the collagenous gel as a result of its exposure to radiation. There has been noticed increased predisposition to proteolytic attack, which could influence favourably the healing process of wounds treated with said collagenous gel. However, the aforesaid method cannot be used for producing, e.g., transplantation grafts (cf. "Problemy techniki w medycynie", t.XII, N 3, 1981, S. Bartelik, "Wpływ sterylizasji radiacyjnej na niektóre włá sciwósci fizyko-chemiczne zelu kolagenowego") of an arbitrary volumetric shape with predetermined mechanical strength, and degree of swelling, and enzymic resistance, since in the aforesaid radiation dose destruction of collagen fibrils occurs in the presence of atmospheric oxygen.

Known in the present state of the art is a method for making ophthalmologic collagen coatings (SU, A, No. 1,321,420), consisting in that the sclera of farm animals is subjected to an alkali-salt treatment, the thus-obtained tissue is homogenized by an aqueous solution of an organic acid, e.g., acetic acid until a collagen solution is formed, which is then rid of low-molecular impurities by way of dialysis against a buffer solution and the pH value of the solution is brought to 4.5 or 7.5, whereupon the resultant collagen solution is evaporated dry and simultaneously spherical coatings are formed therefrom that follow the curvature of the anterior eye portion.

However, the thus-obtained collagen coatings suffer from low mechanical strength, a small degree of swelling and are readily resorbable. Besides, arbitrarily shaped volumetric implants cannot be made by the aforesaid method, since only drying can be resorted to for their formation.

SUMMARY OF THE INVENTION

It is an object of the present invention to provide such a process for producing a cross-linked biopolymer based on collagen and adapted for use in ophthalmological practice that imparts sufficient mechanical strength to said biopolymer, a high degree of swelling and enzymic resistance, as well as an implant made from said biopolymer and aimed at hermetization of corneal and scleral wounds involved in eye injuries and a method for producing said implant, which would ensure a preset shape and size to attain complete wound hermetization and would retain optimum biopolymer properties.

This object is accomplished by a process for producing a cross-linked biopolymer based on collagen and aimed at use in ophthalmological practice, said process consisting in an alkali-salt treatment of the animal sclera, homogenization of the thus-obtained tissue with an aqueous solution of an organic acid until a collagen solution is obtained, followed by extracting low-molecular impurities therefrom, wherein, according to the invention, the collagen solution free of impurities is saturated with nitrous oxide and its concentration is brought to as high as 80 mass percent, whereupon the resultant collagen solution is exposed to an ionizing radiation in a dose of 0.5 to 15 kGy until a cross-linked polymer is formed.

Appropriate selection of the radiation dose, concentration of the collagen solution, and nitrogen protoxide as a cross-linkage promotor provide for uniform cross-linking of the resultant biopolymer over the entire volume of its collagen. Uniformity of cross-linking and an adjustable degree of the latter make it possible to retain elasticity of the resultant biopolymer and to increase its mechanical strength and the degree of its swelling and enzymic resistance twofold. Freedom of the biopolymer from harmful impurities and its collagenous base ensure its good biocompatibility with the eye tissues.

To attain higher quality of the cross-linked biopolymer by eliminating any possibility of forming voids or cavities in its structure, it is recommendable to subject the collagen solution to partial degassing by its centrifugation at 3 to $40 \cdot 10^3$ rpm for 10 to 30 minutes before its exposure to an ionizing radiation.

There is proposed also an implant for hermetization of corneal and scleral wounds involved in eye injuries, said implant being made from the collagen-based cross-linked biopolymer, according to the invention. It is due to its high degree of swelling and a possibility of adjusting said degree of swelling, as well as due to an adequate strength of the implant biopolymer that said implant is capable of ensuring complete hermetization of wounds involed in eye injuries without application of any addiional means that will be traumatic to the eye.

This object is accomplished also by a method for producing said implant, comprising an alkali-salt treatment of the animal-origin sclera, homogenization of the thus-obtained tissue with an aqueous solution of an organic acid until a collagen solution is formed, followed by extraction of low-molecular impurities therefrom, wherein, according to the invention, the concentration of the collagen solution free of impurities is brought to 0.2 to 1.3 mass percent and is saturated with nitrous oxide, whereupon a mold is filled with said collagen solution and the latter is exposed to an ionizing radition in a dose of 0.5 to 15 kGy, the resultant blank for an implant from a cross-linked polymer is subjected to dialysis with water for 24 to 48 hours and dried until the moisture content of the cross-linked biopolymer equals 30 to 50 mass percent, whereupon the blank is given the shape and size of the desired implant that provide complete hermetization of corneal and scleral wounds involved in eye injuries.

Such a method makes it possible to adjust the parameters of the biopolymer properties, as well as its shape and size, which is an indispensable prerequisite of its application.

For optimization of the parameters of the implant properties it is expedient to subject it to partial degassing, before placing the collagen solution in the mold, by consecutive freezing, thawing at 20 to 25° C. and centrifugation at 1 to $2 \cdot 10^3$ rpm for 10 to 60 minutes.

For more convenience in placing the implant in an eye would it be desirable that it be shaped as a cylinder 3 to 5 mm long with its base having a diameter of 0.5 to 4.0 mm and that said cylinder have a tapered end.

There is also proposed a method for hermetization of corneal or scleral wounds involved in eye injuries, wherein, according to the invention, said implant made of a collagen-based cross-linked biopolymer and shaped as cylinder having a tapered end is introduced, with its tapered end, into the operative wound incision, said implant is fixed in the wound for 1 or 2 minutes in order to ensure the proper contact of the wound lips with the implant cylindrical surface, and that implant portion which stands over the corneal or scleral surface is removed.

The proposed method cuts down the operation time, reduces the degree of traumatic lesion of the eye operated upon and rules out any danger of a post-operative complication, such as stitch abscess or dehiscence of an imperfectly applied suture. The method, according to the invention, makes it possible to effect hermetization of lacerated and flap wounds of the cornea and sclera having infected or cut-off edges.

DETAILED DESCRIPTION OF THE INVENTION

The process for producing a collagen-based cross-linked biopolymer, according to the invention, is carried into effect as follows.

The sclera of farm animals is subjected to an alkali-salt treatment, whereupon it is thoroughly rid of internal eye tunics, residues of the conjunctiva and muscles, and the stroma is isolated and cut into small pieces. Then an accurately weighed portion of the stromal tissue is washed with distilled water till complete removal of mechanical impurities and blood, transferred into a flask into which is poured with a sodium hydroxide solution in a saturated sodium sulphate solution (500 ml per 10 g of the tissue) and allowed to stand at 18° to 20° C. for 48 hour. Next the solution is decanted an dthe tissue is neutralized to the pH value of 6.0 to 7.0 by mixing it with a 2 percent boric acid solution and changing said solution many times. Thereupon the tissue is washed with distilled water till complete elimination of a sulphate ion from the wash liquor. The thus-obtained tissue is subjected to homogenization by placing it in a 1M solution of an organic acid, e.g., acetic, citric, or ascorbic so that the final protein concentration in the solution be equal to 1 mass percent. Then the mass is agitated and allowed to stand in a cooler at a lower temperature for one to three days. Next the homogeneous mass is centrifugated and allowed to stand at a lower temperature for 24 hours. The resultant collagen solution is passed through filter. To extract low-molecular impurities therefrom an acetate solution of collagen is diluted with acetic acid till a protein concentration of 0.7 to 0.8 mass percent, and dialyzed against a phosphate or citrate buffer at 18° to 20° C. in order to bring the pH value to 4.5 to 7.5. Then a beaker is filled with the collagen solution and placed in a vacuum chamber in order to eliminate atmospheric oxygen, which is in fact an inhibitor of the following irradiation process, whereupon the collagen solution is centrifugated. The resultant collagen solution is saturated with chemically pure nitrous oxide, which is in effect a non-toxic promotor of collagen cross-linkage. Thereupon the concentration of the solution is brought to maximum 80 mass percent, which proves to be an ultimate concentration, since otherwise the cross-linked biopolymer obtained lacks strength after having swollen. It is recommended that in order to upgrade the quality of the resultant cross-linked biopolymer, i.e., to rule out formation of voids or cavities therein with the resultant reduction of its mechanical strength, the biopolymer should be subjected to partial degassing by means of centrifugation at 3 to $40 \cdot 10^3$ rpm for 10 to 30 minutes, which is quite sufficient for complete removal of excess nitrous oxide in keeping with the concentration of the collagen solution. Then the collagen solution is exposed to an ionizing radiation in a dose of 0.5 to 15 kGy at room temperature until the desired cross-linked biopolymer is obtained. When the radiation dose is below 0.5 kGy the resultant biopolymer possesses a mechanical strength which is too low and enzymic resistance, whereas with the radiation dose exceeding 15 kGy the resultant biopolymer losses elasticity and becomes brittle. The thus-obtained cross-linked biopolymer is subjected to dialysis in distilled water for one to three days to remove acetic acid therefrom. The wash liquor should have the pH value below 6.3. The thus-purified cross-linked biopolymer is placed in distilled water, hermetically sealed and sterilized.

The method for producing an implant from the cross-linked biopolymer, according to the invention, for hermetization of corneal and scleral wounds involved in eye injuries, is carried into effect as follows.

An alkali-salt treatment of the farm animals' sclera, homogenization of the thus-obtained tissues with an aqueous solution of an organic acid, extraction of low-molecular impurities from the resultant collagen solution are effected as described herein-before. The resultant collagen solution is either diluted or concentrated so as to bring its concentration to 0.2 to 1.3 mass percent, thus ensuring for the implant biopolymer an optimum mechanical strength and ability to swell rapidly, as well as good elastic properties. Then the collagen solution is transferred into a beaker and subjected to vacuumization and centrifugation to eliminate as much atmospheric oxygen as possible. Next chemically pure nitrous oxide is made to bubble through the resultant collagen solution under constant stirring until it gets completely saturated with nitrogen protoxide. In order to partially degas the solution it is expedient to freeze it in a cooler and then to thaw the solution at a slow rate at room temperature (20° to 25° C.), whereupon to centrifugate the solution at 1 to 2·10³ rpm for 10 to 60 minutes. The aforestated conditions having been fully satisfied, complete removal of excess nitrous oxide is assured, while said excess amount of gas might result in formation of voids in the structure of the cross-linked biopolymer the implant is made from. Further on a mold is filled with the collagen solution and the latter is exposed to an ionizing radiation at a dose of 0.5 to 15 kGy. The thus-formed blank from the collagen-based cross-linked biopolymer is subjected to dialysis in distilled water to the pH value of 6.5 to 7.0 for 24 to 48 hours. The thus-treated blank is dried until the moisture content of said biopolymer equals 30 to 50 mass percent, which will ensure a 7- to 10 fold degree of swelling of the implant when used for hermetization of eye wounds. The dried blank is subjected to freezing at a fast rate in liquid nitrogen and lyophilized for 48 hours, whereupon the stiff blank is given the shape and size of the desired implant, which will assure complete hermetization of corneal and scleral wounds. It is expedient that the implant be shaped as a cylinder with a tapered end, said cylinder der being 3 to 5 mm long and its base having a diameter of 0.5 to 4.0 mm. Such a shape of the implant will provide maximum convenience in its being introduced into the operative wound incision in the eye, the length of the implant is so selected as to make surgeon's manipulations convenient, while the diameter will ensure a required extent of contact of the would lips with the surface of the cylindrical implant when the latter is being fixed to the wound.

Given below are specific exemplary embodiments of practical implementation of the present invention.

EXAMPLE 1

The scleral stroma cut to pieces and purified, taken in an amount of 20 g is poured with one liter of 10-percent sodium hydroxide in a saturated sodium sulphate solution and is allowed to stand at 18° to 20° C. for 48 hours. Then the solution is decanted, the tissue is washed with a small amount of distilled water, contacted with one liter of a 2-percent boric acid solution and agitated for two hours, while changing the boric acid solution two times within the aforesaid period of time. The tissue is carefully washed with distilled water, under constant stirring, in an amount of 5 liters until the sulphate-ion is completely removed from the wash liquor. The thus-obtained watered tissue in an amount of 250 ml is subjected to homogenization by adding 350 ml of 0.5M acetic acid thereto. Then the mass is agitated and allowed to stand for 24 hours at 4° C., whereupon the homogenous mass is centrifugated at 2·10³ rpm for 30 minutes and is allowed to stand for three days at 4° C. The resultant collagen solution is passed through a glass filter. The protein concentration of said solution equals one mass percent. To extract low-molecular impurities from the collagen solution, its acetate solution is diluted with a 0.5M acetic acid solution till the protein concentration therein becomes equal to 0.8 mass percent, whereupon the solution is dialyzed against a 0.2M citrate buffer at 18° to 20° C. to the pH value of 4.5. Then the collagen solution is vacuumized at room temperature until gas bubbles appear and is centrifugated at 2·10³ rpm for 30 minutes. Next a beaker is filled with the resultant solution and the latter is saturated with chemically pure nitrogen protoxide by bubbling said gas through 20 ml of the solution for 20 minutes at a rate of 5 ml/s. Once the solution has been saturated its partial degassing is carried out by centrifugation at 3·10³ rpm. The saturation and centrifugation process is repeated two times. Thereupon the collagen solution is lyophilized until a concentration of one mass percent is obtained, and is exposed to an ionizing radiation at a dose of 1 kGy. The resultant collagen-based cross-linked biopolymer is taken out of the beaker and subjected to dialysis in distilled water for 24 hours until the pH value of the wash water gets equal to 6.4. Then the cross-linked biopolymer is placed in a vial filled with distilled water and the vial is hermetically sealed, whereupon it is placed in liquid nitrogen at minus 196° C. and exposed to gamma-radiation in a dose of 30 kGy. Next the vial is immersed in a water-filled vessel for 6 or 7 hours at 80° C. for the cross-linked biopolymer to thaw. The thus-treated cross-linked biopolymer is featured by sterility, good mechanical strength and enzymic resistance.

EXAMPLE 2

A nitrous oxide-saturated collagen solution produced as described in Example 1, is subjected to concentration. To this end 6 g of dry collagen films is added thereto per 20 ml of a 0.8-mass percent collagen solution and the latter is homogenized under stirring in a nitrogen atmosphere till a 30-percent collagen solution is obtained. The resultant solution is centrifugated at 2·10³ rpm for 20 minutes and transferred into a beaker, whereupon the solution is exposed to an ionizing radiation in a dose of 10 kGy. The resultant collagen-based cross-linked bipolymer is placed in a beaker filled with a 10-percent aqueous formalin solution for 2 hours in order to increase hydrophobic properties of the biopolymer. Then said biopolymer is subjected to dialysis in distilled water for two days until the pH value of the wash water is equal to 6.7. Next the biopolymer is sterilized as descirbred in Example 1, with the exception that a dose of gamma-irradiation applied is 15 kGy. The thus-obtained collagen-based cross-linked biopolymer is sterile, possesses good mechanical strength and enzymic resistance.

EXAMPLE 3

A collagen solution saturated with nitrous oxide and prepared as described in Example 1 is subjected to concentration. To this aim the collagen solution is dehydrated in a mold immersed in Sefadex G-10 in a nitrous oxide atmosphere. The dehydration process is judged by change in the weight of the collagen solution in one half of the mold so that a next portion be added as soon as the weight of the solution is decreased 100 times. The abovesaid operation is repeated until the entire mold is filled with a 80-percent collagen solution. Then the mold filled with the solution is transferred into the tray of a centrifugal machine and the solution is centrifugated at 40·10³ rpm, whereupon the mold is closed with its other half and the solution is exposed to gamma-radiation in a dose of 15 kGy. The resultant collagen-based cross-linked biopolymer is subjected to dialysis in distilled water for three days until the pH value of wash water equals 6.8. Sterilization of the biopolymer is carried out as in Example 1, with the sole exception that a dose of gamma-radiation applied is 30 kGy. The thus-treated cross-linked biopolymer is sterile, features good mechanical strength and enzymic resistance.

EXAMPLE 4

The scleral stroma taken from farm animals, purified and cut to pieces in an amount of 20 g is poured with one liter of 10-percent sodium hydroxide in a saturated sodium sulphate solution and is allowed to stand at 18° to 20° C. for 48 hours. Then the solution is decanted, the tissue is contacted with one liter of a 2-percent boric acid solution and the resultant mixture is stirred for two hours, while changing the boric acid solution two times. The tissue is carefully washed with distilled water in an amount of 5 liters under constant stirring until the sulphate-ion is completely eliminated from the wash liquor. Homogenization of 250 ml of the thus-obtained watered tissue is carried out by adding some 0,5M acetic acid, stirring and allowing the mixture to stand for 24 hours at 4° C. Then the homogeneous mass is centrifuged at $2 \cdot 10^3$ rpm and allowed to stand for three days at 4° C. The resultant collagen solution passed through a glass filter, contains one mass percent of collagen. Said solution is diluted with 0.5M acetic acid down to a concentration of 0.8 mass percent and is dialyzed against a 0.5M phosphate buffer at 18° to 20° C. until the pH value equals to 7.0. Then the 0.8-mass percent collagen solution is diluted to a four-times lower concentration (0.2 mass percent) with 0.25M acetic acid, vacuumized at room temperature until gas bubbles appear and centrifuged at $1 \cdot 10^3$ rpm for 60 minutes. The thus-obtained collagen solution is saturated completely with chemically pure nitrous oxide and centrifugated at $1 \cdot 10^3$ rpm for 60 minutes for undissolved gas to be removed. Then said solution is frozen by being placed in a cooler for 24 hours, whereupon it is allowed to thaw at room temperature and centrifugated at $1 \cdot 10^3$ rpm. The resultant collagen solution is transferred, with the aid of a peristatic pump, to a dia. 0.5 mm capillary and is exposed to an ionizing radiation in a dose of 15 kGy at room temperature. The thus-formed collagen-based cross-linked biopolymer shaped as a cylinder is subjected to dialysis for 24 hours at room temperature until the pH value of the wash water equals 6.4. Then a cylindrical-shaped blank is hung in a dust-free cabinet drier to be dried three hours at room temperature until its biopolymer features the moisture content of 30 mass percent. Then the blank is frozen in liquid nitrogen at a fast rate and is placed in a liophilizer, wherein drying is carried out for 7 hours. Next 3-mm long cylinders with a tapered end are cut out of the thus-treated blank, using a razor blade. The finished implant for hermetization of corneal and scleral wounds is packed in hermetically sealed vials and sterilized with gamma-radiation in a dose of 25 kGy. The cross-linked biopolymer of the implant is sterile, has good mechanical strength and enzymic resistance and is optically transparent.

EXAMPLE 5

A solution featuring a collagen concentration of 0.8 mass percent is prepared as described in Example 4. Further on the collagen solution is centrifugated at $12 \cdot 10^3$ rpm for 30 minutes and is saturated with nitrous oxide, whereupon the solution is centrifugated again at $2 \cdot 10^3$ rpm. In view of partial degassing, the collagen solution is frozen in a cooler for 24 hours and is thawed at room temperature, then is centrifugated at $2 \cdot 10^3$ rpm for 30 minutes, the resultant solution is poured into a dia. 4-mm cylindrical mould and exposed to an ionizing radiation at a dose of 5 kGy. The thus-obtained blank from the cross-linked biopolymer based on collagen is placed in distilled water for 48 hours, while changing the water until the pH value of the waste water equals 6.8. Then the blank is hung at one end in a dust-free cabinet drier to dry there at room temperature until the moisture content of its biopolymer gets equal to 50 mass percent, whereupon the blank is frozen in liquid nitrogen and is placed in a lyophilizer for 7 hours. Next 4-mm long cylinders with a tapered end are cut out of the blank. The thus-obtained implant for hermetization of corneal and scleral wounds is packed in hermetically sealed vials and sterilized with gamma-radiation in a dose of 25 kGy. The cross-linked biopolymer of the implant is sterile, feature good mechanical strength and enzymic resistance.

EXAMPLE 6

A solution with a collagen concentration of 0.8 mass percent is prepared as described in Example 4. The solution is then concentrated in the AMICON unit with the XM50 filter, while concentration process is judged by a reduced level of the solution in the tray of the unit. The resultant solution having a collagen condentration of 1.3 mass percent is vacuumerized until gas bubbles appear, and centrifugated at $2 \cdot 10^3$ rpm for 30 minutes. Then the collagen solution is frozen at a slow rate in a coller for 24 hours and is thawed at room temperature, whereupon it is centrifugated again at $2 \cdot 10^3$ rpm for 30 minutes. The thus-treated solution is poured into a dia. 2-mm cylinder-shaped mold and exposed to an ionizing radiation in a dose of 0.5 kGy. The thus-obtaiuned cross-linked biopolymer in the form of a cylinder-shaped blank is subjected to dialysis in distilled water for 48 hours until the pH value of the waste water equals 6.8. Then the blank is hung at one end in a dust-free cabinet drier and is let to concentrate at room temperature until the moisture content of its biopolymer become equal to 50 mass percent. Next the blank is frosen in liquid nitrogen and placed in a lyophilizer for 8 hours, whereupon the blank is cut into 5-mm long cylinders with a tapered end. The resultant implant for hermetization of corneal and scleral wounds is packed in hermetically sealed vials and sterilized with gamma-radiation in a dose of 30 kGy. The cross-linked biopolymer of the implant is sterile, possesses good mechanical strength and enzymic resistance.

EXAMPLE 7

An implant prepared according to Example 4 and shaped as a cylinder with a tapered end, said cylinder being 3 mm long and featuring the diameter of its base equal to 0.5 mm, is introduced, with its tapered end, into a 1-mm long incision of the corneal operative wound. Then the implant is fixed in the wound for 1.5 minutes with a forceps pinching the implant at its free end so as to provide a full contact of the wound lips with the cylindrical implant surface. The implant portion standing over the corneal surface is removed. Thus, complete hermetization of the wound is attained, the absorption period being 20 days. Histologic examinations detected no postoperative complications.

EXAMPLE 8

An implant prepared according to Example 5 and shaped as a dia. 4 mm cylinder with a tapered end and a diameter of its base equal to 4 mm, is introduced, with its tapered end, into a 4-mm long incision of the scleral wound and is fixed in the wound for 2 minutes by being pinched with a forceps at its free end. As a result, a full contact of the wound lips with the implant cylindrical surface is attained. The implant portion standing above the scleral surface is removed. Thus, complete hermetization of the wound is attained, the absorption period being 20 days. No postoperative complications were revealed by histologic examinations.

EXAMPLE 9

An implant prepared according to Example 6 and shaped as a dia. 5 mm cylinder with a tapered end and a diameter of its base equal to 2 mm, is introduced, with its tapered end, into a 2-mm long operative wound incision at the eye limbus and is fixed in the wound for 1.5 minutes by being pinched with a forceps at its free end. As a result, a full contact of the wound lips with the implant cylindrical surface is attained. The implant portion standing over the lumbus is removed. Thus, complete hermetization of the wound is attained, the absorption period being 16 days. No postoperative complications were revealed by histologic examinations.

What we claim is:

1. A process for producing a collagen-based cross-linked biopolymer for ophthalmological uses, comprising:
   alkali-salt treatment of animals' sclera;
   homogenization of the thus-obtained tissue with an aqueous solution of an organic acid until a collagen solution is formed;
   extraction of low molecular impurities from the collagen solution;
   saturation of said solution with nitrous oxide;
   brining the concentration of said collagen solution to 80 mass percent maximum;
   exposure of said collagen solution to an ionizing radiation in a dose of 0.5 to 15 kGy until a cross-linked biopolymer is formed.

2. A process as claimed in claim 1, wherein the collagen solution is subject, prior to irradiation, to partial degassing by its centrifugation at 3 to $4 \cdot 10^3$ rpm for 10 to 30 minutes.

3. An implant for hermetization of corneal and scleral wounds involved in eye injuries, said implant being made from the collagen-based cross-linked biopolymer produced according to the process of claim 1.

4. A method for producing an implant for hermetization of corneal and scleral wounds involved in eye injuries as claimed in claim 3, comprising:
   alkali-salt treatment of animals' sclera;
   homogenization of the thus-obtained tissue with an aqueous solution of an organic acid until a collagen solution is formed;
   extraction of low-molecular impurities from the collagen solution;
   bringing the concentration of said solution to 0.2 or 1.3 mass percent;
   saturation of said collagen solution with nitrous oxide;
   filling a mold with said collagen solution and exposure of said solution to an ionizing radiation in a dose of 0.5 to 15 kGy until a blank is formed for an implant made from the collagen-based cross-linked biopolymer;
   subjecting said blank made from the cross-linked biopolymer to dialysis with water for 24 to 48 hours;
   drying said blank until the moisture content of its cross-linked biopolymer equals 30 to 50 mass percent;
   imparting to said blank the shape and size of an implant so as to ensure complete hermetization of corneal and scleral wounds involved in eye injuries.

5. A method as claimed in claim 4, wherein the collagen solution before being placed in a mold is subjected to partial degassing by way of consecutively performed freezing, thawing at 20° to 25° C. and centrifugation at 1 to $2 \cdot 10^3$ rpm for 10 to 60 minutes.

6. A method for hermeitization of corneal or scleral wounds involved in eye injuries, comprising:
   introducing an implant as claimed in claim 3, made from the collagen-based cross-linked biopolymer and shaped as a cylinder with a tapered end, with said tapered end, into an operative wound incision;
   fixing said implant in the wound for 1 to 2 minutes in order to ensure a contact of the wound lips with the implant cylindrical surface and ;
   removing the implant portion that stands over the corneal or scleral surface of the eye.

7. A method as claimed in claim 6, wherein the implant is shaped as a cylinder with a tapered end, said cylindrical being 3 to 5 mm long and having its base diameter of 0.5 to 4 mm.

8. A product of the process of claim 1.

9. A product of the process of claim 2.

* * * * *